(12) United States Patent
Stierli

(10) Patent No.: US 9,804,111 B2
(45) Date of Patent: Oct. 31, 2017

(54) IMPEDANCE-BASED MEASUREMENT DEVICE WITH A TWO-DIMENSIONAL ARRAY OF COILS

(71) Applicant: PROCEQ SA, Schwerzenbach (CH)

(72) Inventor: Peter Stierli, Uerikon (CH)

(73) Assignee: PROCEQ SA, Schwerzenback (CH)

( * ) Notice: Subject to any disclaimer, the term of this patent is extended or adjusted under 35 U.S.C. 154(b) by 175 days.

(21) Appl. No.: 14/760,565

(22) PCT Filed: Jan. 14, 2013

(86) PCT No.: PCT/CH2013/000008
§ 371 (c)(1),
(2) Date: Jul. 13, 2015

(87) PCT Pub. No.: WO2014/107816
PCT Pub. Date: Jul. 17, 2014

(65) Prior Publication Data
US 2015/0355121 A1 Dec. 10, 2015

(51) Int. Cl.
*G01R 27/28* (2006.01)
*G01N 27/02* (2006.01)
(Continued)

(52) U.S. Cl.
CPC ......... *G01N 27/025* (2013.01); *G01N 27/904* (2013.01); *G01N 33/383* (2013.01);
(Continued)

(58) Field of Classification Search
CPC .. G01R 27/26; G01R 27/2611; G01R 27/267; G01R 27/00; G01L 21/30; G01N 27/62; G01N 27/64; H01J 41/00; H01J 41/02
(Continued)

(56) References Cited

U.S. PATENT DOCUMENTS 6,819,121 B1   11/2004  Hager, III et al.
2002/0190724 A1 * 12/2002  Plotnikov ............ G01N 27/904
                                                      324/529
(Continued)

FOREIGN PATENT DOCUMENTS

CH    669 843       4/1989
CN    1035894       9/1989
(Continued)

OTHER PUBLICATIONS

DE 102008056416 Machine Translation, May 27, 2010.*
China Search Report conducted in counterpart China Appln. No. 201380070352.8 (Feb. 23, 2017) (w/ English translation).

*Primary Examiner* — Huy Q Phan
*Assistant Examiner* — Raul Rios Russo
(74) *Attorney, Agent, or Firm* — Greenblum & Bernstein, P.L.C.

(57) ABSTRACT

The device for the impedance-based probing of materials described herein comprises a two-dimensional array of coils (1) and a measurement unit (4) adapted to determine, for each coil (1), a parameter indicative of its impedance. A pulse generator (3) is able to generate current pulses in each coil (1). The circuitry drives and senses the coil array through row and column lines (rp1 ... rpN1, cp1 ... cpN2, c21 ... csN2) in order to minimize the number of required components. The device can, in particular, be used for probing concrete.

16 Claims, 3 Drawing Sheets

(51) Int. Cl.
  *G01R 27/26* (2006.01)
  *G01N 27/90* (2006.01)
  *G01N 33/38* (2006.01)
  *G01L 21/30* (2006.01)

(52) U.S. Cl.
  CPC .......... *G01R 27/26* (2013.01); *G01R 27/2611* (2013.01); *G01L 21/30* (2013.01)

(58) Field of Classification Search
  USPC .......... 324/76.11–76.83, 459, 600, 649, 654
  See application file for complete search history.

(56) References Cited

U.S. PATENT DOCUMENTS

| | | |
|---|---|---|
| 2007/0126422 A1 | 6/2007 | Crouch et al. |
| 2008/0150370 A1* | 6/2008 | Heuermann ............ G04F 1/005 307/110 |
| 2009/0108844 A1* | 4/2009 | Sodickson ........... A61B 5/0536 324/309 |
| 2011/0163740 A1* | 7/2011 | Russell .................. G01N 27/72 324/220 |
| 2012/0074932 A1* | 3/2012 | De Smet ............ G01N 27/9046 324/240 |
| 2014/0369079 A1* | 12/2014 | Koch ...................... H02M 1/08 363/17 |

FOREIGN PATENT DOCUMENTS

| | | |
|---|---|---|
| CN | 101246116 | 8/2008 |
| CN | 101821683 | 9/2010 |
| CN | 102832836 | 12/2012 |
| DE | 10 2008 056 416 | 5/2010 |
| EP | 2 182 347 | 5/2010 |
| JP | 4710061 | 6/2011 |
| WO | 90/06488 | 6/1990 |
| WO | 2007/056679 | 5/2007 |

\* cited by examiner

IMPEDANCE-BASED MEASUREMENT DEVICE WITH A TWO-DIMENSIONAL ARRAY OF COILS

CROSS-REFERENCE TO RELATED APPLICATION

This application is a U.S. National Stage of International Application No. PCT/CH2013/000008 filed Jan. 14, 2013.

TECHNICAL FIELD

The invention relates to a device for the electrical impedance probing of materials that has at least one coil, a pulse generator for generating current pulses in said coil and a measurement unit for determining a parameter indicative of the impedance of said coil.

BACKGROUND ART

It has been known to probe materials, such as reinforced concrete, by electrical impedance measurement devices. Such devices comprise a coil and a pulse generator for feeding current pulses to the coil. After each current pulse, the magnetic field generated by the coil decays and gives rise to a decaying induction voltage over the coil. The decay of this voltage is a function of the coil's impedance, which depends on the permeability $\mu$ and conductivity $\sigma$ of the material within the field's reach. For example, if the coil is close to a metallic reinforcement bar embedded within the concrete, the average permeability $\mu$ and conductivity $\sigma$ within the field's reach and therefore the impedance of the coil is changed, which leads to a slower decay of the induction voltage.

Hence, by measuring a parameter indicative of the inductance of the coil, it is possible to gain insight into the composition of the material adjacent to the coil. This is particularly useful for determining the location, depth and/or diameter of reinforcement bars or other metal parts within concrete.

DISCLOSURE OF THE INVENTION

The problem to be solved by the present invention is to further improve this type of device. This problem is solved by the device of claim 1. Accordingly, the device comprises a two-dimensional array of coils. Further, the measurement unit is adapted to determine a parameter indicative of the impedance of a coil for individual ones of said coils. Such a design allows to provide a spatially resolved measurement of the material, e.g. for locating the position and/or orientation of a reinforcement bar or another metal part in concrete.

In an advantageous embodiment, the pulse generator is adapted to feed individual current pulses to each one of said coils, i.e. it is possible to feed a current pulse to each selected coil without feeding pulses to other coils. This allows to generate a well-localized magnetic field at any location within the array.

Further, the measurement unit can be adapted to measure said parameter e.g. for individual ones of said coils.

The coils can advantageously be formed by conductive tracks on a printed circuit board, which allows to manufacture them at low cost.

The device is advantageously used for probing concrete, in particular for probing reinforced concrete in order to locate reinforcement bars or other metal parts therein.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE INVENTION

Definitions

The term "two dimensional array of coils" is to be understood such that the coils are arranged in a matrix on a flat or curved plane with a first number $N1>1$ of said coils arranged side by side along a column direction and a second number $N2>1$ of said coils arranged side by side along a column direction, with the row and column directions extending transversally to each other.

The term "device for an impedance-based probing of materials" is to be understood as a device for determining properties of a sample material, such as concrete, by means of coils being brought into proximity of the material. Current pulses are fed to the coils, and the build-up or decay of the magnetic field of the coils is a function of the permeability $\mu$ and conductivity $\sigma$ as seen by the field, which depends on the composition of the material. Hence, the device is adapted to determine a property depending on the permeability $\mu$ and/or conductivity $\sigma$ of the material.

Figure 1:
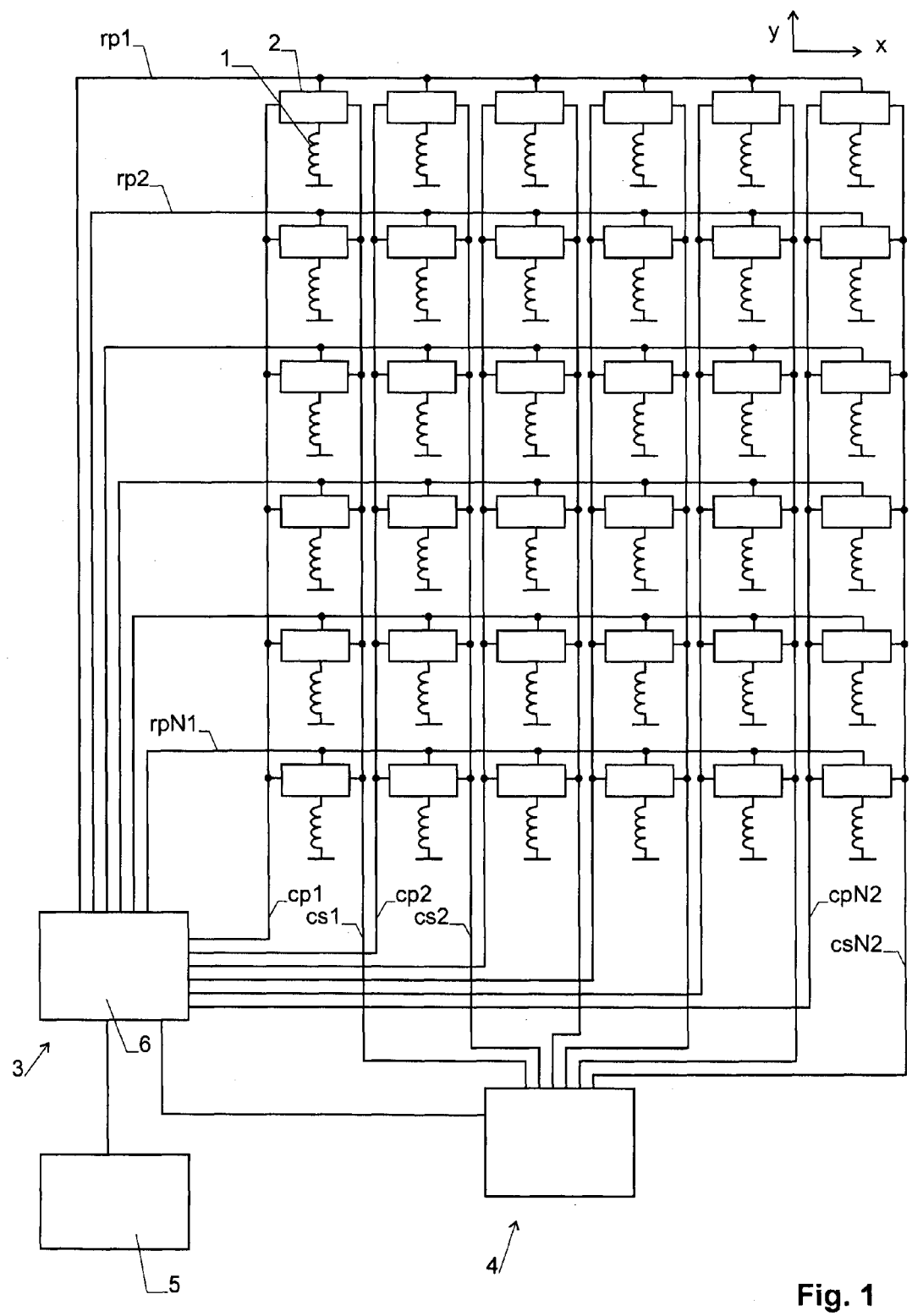
FIG. 1 shows a block diagram of the components of a device.

Overview:

FIG. 1 shows an overview of the components of a device according to the present invention. As can be seen, the device comprises a plurality of coils 1 arranged in a two dimensional array arranged in rows and columns, as denoted by the row direction x and the column direction y. Albeit the number N2 of coils in each row and the number N1 of coils in each column can be as low as 2, advantageously both these numbers are larger than 2 in order to gain spatially well resolved information for the material to be tested. In the embodiment of FIG. 1, N1=N2=6, but other numbers, such as 8 or 16 can be used as well.

A coil circuit 2 is attributed to each coil 1. Further, the device comprises a pulse generator 3, a measuring unit 4 and a control unit 5. Pulse generator 3 is adapted to feed individual current pulses to each one of the coils 1, while measuring unit 4 is able to determine, for each coil, a parameter indicative of its impedance. Control unit 5 coordinates the operation of pulse generator 3 and measuring unit 4. The design of these components will be described in more detail in the next sections.

Pulse Generator:

Pulse generator 3 comprises row pulse lines rp1 . . . rpN1 and column pulse lines cp1 . . . cpN2, all of which are connected to a timing circuit 6. In each cell i, j of the two-dimensional array, one column pulse line cpi intersects with one row pulse line rpj. In operation, one of the row pulse lines is e.g. set to a high potential (such as 10 Volts), while the others are kept at a low potential (such as 0 volts).

Further, the column pulse lines are kept at a high potential (such as 10 Volts), with the exception of one, to which at least one low potential pulse (e.g. to 0 volts) is applied.

Figure 2:
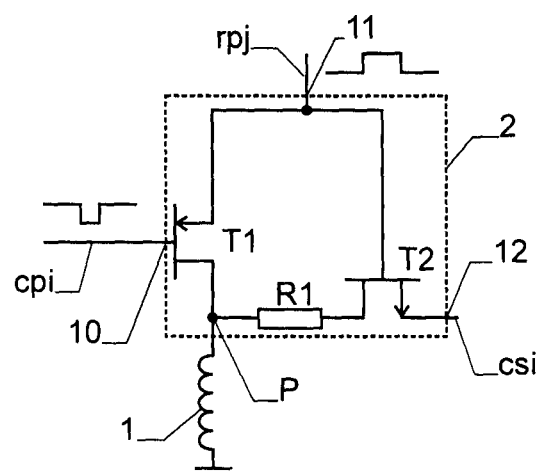
FIG. 2 shows an embodiment of the coil circuit.

Coil Circuits:

FIG. 2 shows an embodiment of a single coil circuit 2 and its attributed coil 1. As can be seen, coil circuit 2 comprises a first input 10 connected to column pulse line cpi, a second input 11 connected to row pulse line rpj, and an output connected to a column signal line csi, assuming that i and j are the coordinates of the coil circuit within the two-dimensional array of the coils.

Further, each coil circuit 2 comprises a first semiconductor switch T1 and a second semiconductor switch T2, i.e. one first semiconductor switch T1 and one second semiconductor switch T2 are attributed to each coil 1. Both of these switches can e.g. be FETs or bipolar transistors. Each of them has two current terminals (such as the source and drain for an FET or the collector and emitter of a bipolar transistor) as well as a control terminal (such as the gate for an FET or the base for a bipolar transistor). As known to the skilled person, the conductivity between the first and second current terminal is controlled by the voltage at the control terminal, which allows to switch the current between the current terminals on or off by changing the voltage at the control terminal.

As can be seen, one terminal of coil 1 is connected to ground (or to another fixed reference potential), while the other terminal of coil 1 (at point P) is connected to one of the current terminals of semiconductor switch T1. The second current terminal of semiconductor switch T1 is connected to row pulse line rpj. The control terminal of semiconductor switch T1 is connect to column pulse line cpi.

Further, as mentioned, coil circuit 2 comprises a second semiconductor switch T2, whose control terminal is connected to row pulse line rpj, whose one current terminal is connected, via a resistor R1, to coil 1, and whose second current terminal is connected to column signal line csi. Resistor R1 has a resistance of at least 10-1000Ω.

Figure 3:
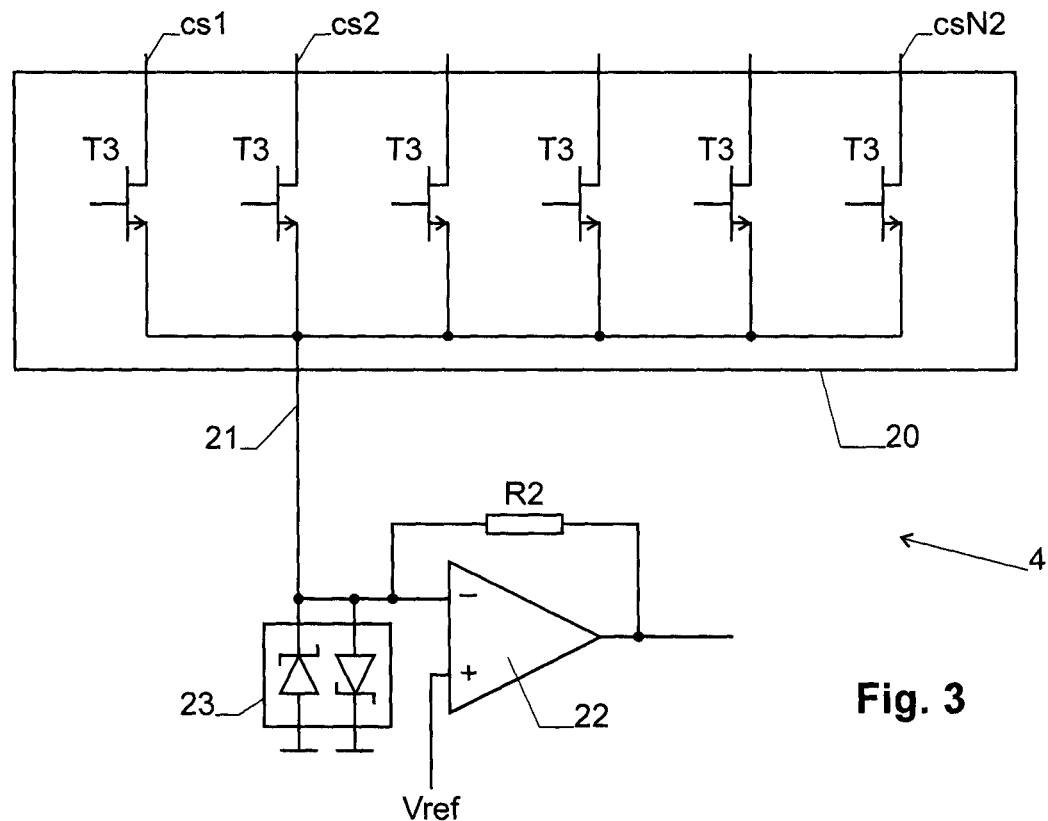
FIG. 3 shows an embodiment of the most important components of the measuring unit.

Measurement Unit:

The design of measurement unit 4 is shown in FIG. 3. It comprises an analogue demultiplexer 20 that has N2 inputs connected to the column signal lines cs1 . . . csN2 and an output 21. Semiconductor switches T3 allow to selectively connect each input to output 21. The control terminals of the semiconductor switches T3 are controlled by control unit 5 and pulse generator 3.

The signal from output 21 is fed to the inverting input of an operational amplifier 22, i.e. the demultiplexer is arranged between the column signal lines cs1 . . . csN2 and amplifier 22. Amplifier 22 has a resistor R2 in its feedback loop. The non-inverting input of amplifier 22 is connected to a constant reference potential Vref.

In addition, and as can be seen, a voltage limiter 23, e.g. comprising two reversely-poled, parallel Schottky diodes, is arranged at the input of amplifier 22. It limits the voltage at the input of amplifier 22 to not more than 100 V against ground, in particular to less than 1 V, e.g. to a few 100 mV against ground.

Operation

The operation of the above embodiment of the device is described in the following.

In normal operation, control unit 5 operates pulse generator 3 to generate a series of pulses on the row and column pulse lines, rp1 . . . rpN1 and cp1 . . . cpN2, respectively, thereby activating individual coils 1 in the coil matrix.

To activate e.g. coil at row j and column i, pulse generator 36 sets all row pulse lines except row pulse line rpj to low potential, while row pulse line rpj is set to high potential. All column pulse lines cp1 . . . cpN2 are set to high potential. Further, demultiplexer 20 is set to connect only column signal line csj to output 21. In this state, all semiconductor switches T1 are non-conducting, i.e. no current flows through any of the coils 1. In addition, only the semiconductor switches T2 at row j are conducting and demultiplexer 20 connects only the coil at column i of row j to the input of amplifier 22.

Now, pulse generator 3 applies a low potential pulse to column pulse line cpi, thereby bringing semiconductor switch T1 into its conducting state, such that a current begins flow through coil 1 at row j and column i. Once a sufficiently strong magnetic field is built up, column pulse line cpi is set back to its high potential, thereby interrupting semiconductor switch T1. This leads to the immediate build-up of a negative induction voltage at the location of point P. The absolute value of this voltage can be more than 100 Volts and may easily exceed the maximum allowable voltage between the current terminals and the control terminal of second semiconductor switches T2 and T3. However, since these semiconductor switches are in their conducting state and connected to voltage limiter 23, the voltage limiter limits the voltage between the current terminals of semiconductor switches T2 and T3 and their gates to an acceptable value. The voltage between semiconductor switch T2 and point P is drops over resistor R1.

Hence, voltage limiter 23 protects semiconductor switches T2 and T3 from excessive voltages. Another purpose of voltage limiter 23 is to prevent amplifier 22 from being operated in saturation while the voltage over coil 1 is high, thereby keeping the amplifier responsive once its input voltage drops to lower levels.

After its initial peak, the induction voltage starts to decay, with a decay rate dependent on the impedance of coil 1. In order to measure a parameter dependent on the impedance, the output of amplifier 22 is sampled at a time when the voltage at point P has dropped to a fairly low value such that amplifier 22 is in its linear operating range. In that operating range, the amplification of amplifier 22 is given by the ratio R2/R1 and is at least 5, in particular approximately 10.

The voltage at the output of amplifier 22 is measured at a given time after switching off the current through coil 1 and it is used for determining the response of the sample material at the location of cell i, j of the two-dimensional coil array.

It must be noted that, alternatively to using second semiconductor switches T2 and/or demultiplexer 20, the output side (right hand side of FIG. 2) of resistor R1 of all cells in a row, a column, or in the whole matrix, could be directly connected to the input of amplifier 22. However, in this case, the noise amplification of amplifier 22 would be higher due to the lower impedance of its inverting input against ground.

For this reason, it is advantageous to provide the second semiconductor switches T2 and/or the demultiplexer 20 between the coils 1 and amplifier 22 such that amplifier 22 can be connected to measure the induction voltage of one single coil 1 or at least of only a subset of the coils at one time.

Figure 4:
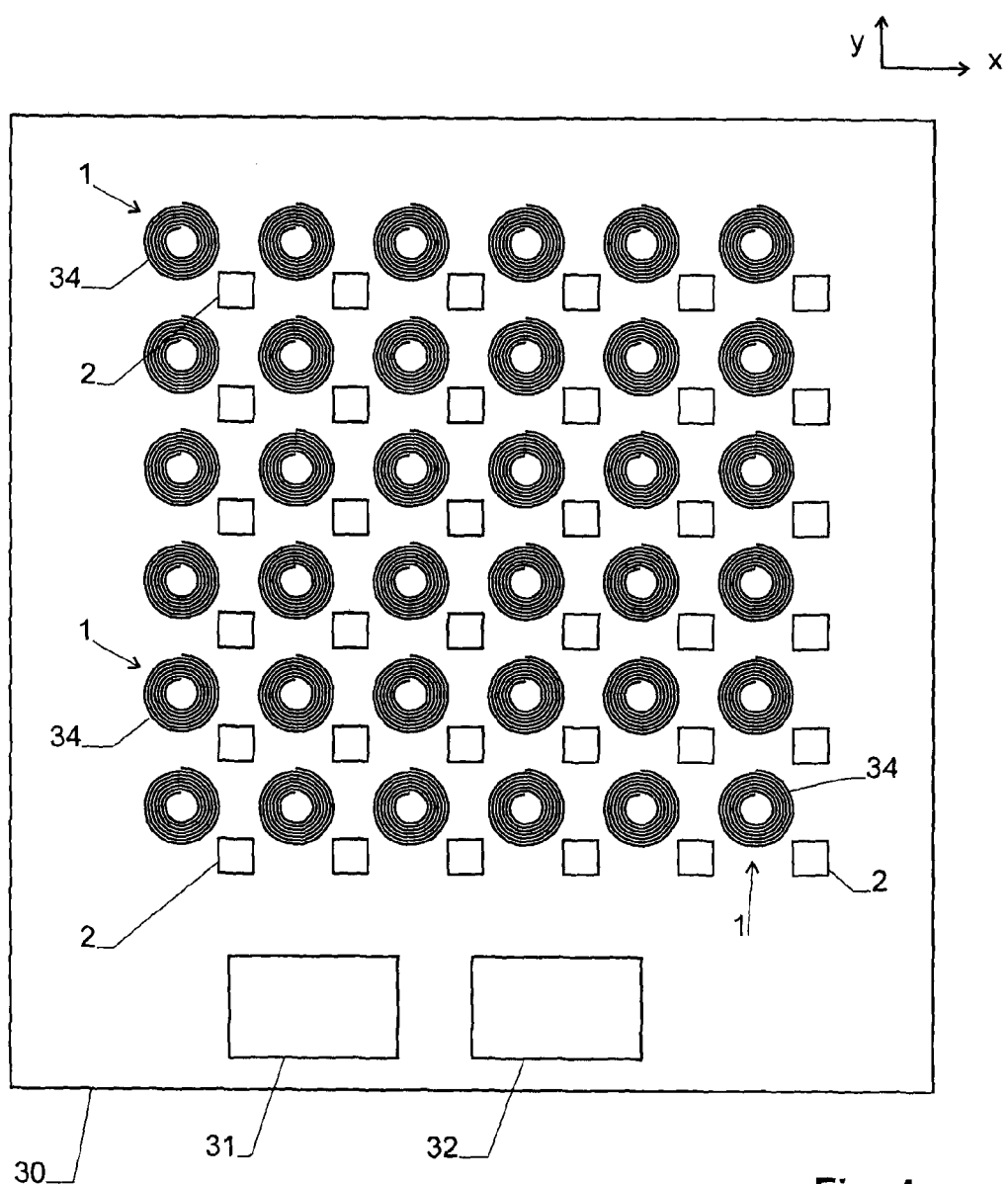
FIG. 4 shows the coils on a printed circuit board and FIG. 5 is an illustration of a coil implemented on a multilayer printed circuit board.
Figure 5:
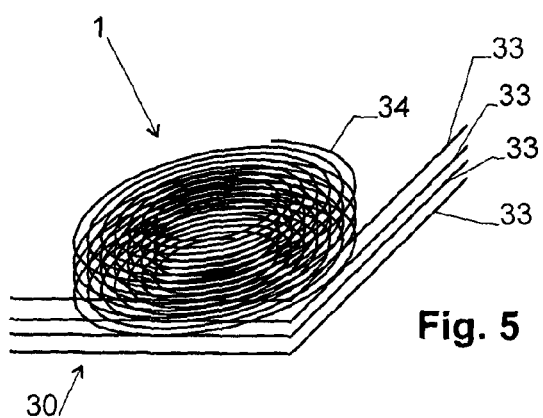

Mechanical Design:

The mechanical design of the device is shown in FIGS. 4 and 5. As can be seen, the coils 1 are advantageously formed by conductive tracks 34 on a printed circuit board 30. They are arranged in a two-dimensional array in rows and columns. They form N1 rows along row direction x and N2 columns along column direction y. As mentioned, N1 and N2 are advantageously larger than 2, e.g. 8, for obtaining a reasonable spatial resolution. The coil circuit 2 of each coil 1 can be arranged adjacent to its coil, also in a two-dimensional array of the same number of rows and columns. Other circuitry, which is identified under reference numbers 31, 32 and which may e.g. include pulse generator 3, control unit 5 and/or measurement unit 4, can e.g. be located at the edge of circuit board 30 or on a separate circuit board.

Circuit board 30 is advantageously a multi-layer circuit board, i.e. it comprises a plurality of layers 33, as schematically illustrated in FIG. 5. As known to the skilled person, each such layer can carry its own metallic tracks. Coil 1 is advantageously formed by conductive tracks 34 on several of the layers 33. Each track 34 forms a spiral, with all spirals being substantially of identical design and wound around a common axis.

Notes:

The device of FIG. 4 shows an embodiment where the row and column directions x, y are perpendicular to each other. They may, however, also be arranged under other angles, such as 60° or 120°.

In summary, the present device for the impedance-based probing of materials comprises a two-dimensional array of coils 1 and a measurement unit adapted to determine, for each coil 1, a parameter indicative of its electrical impedance. Pulse generator 3 is able to generate current pulses in each coil 1. The circuitry drives and senses the coil array through row and column lines rp1 . . . rpN1, cp1 . . . cpN2, cs21 . . . csN2 in order to minimize the number of required components. The device can, in particular, be used for probing concrete, although it can also be used in other applications.

While there are shown and described presently preferred embodiments of the invention, it is to be distinctly understood that the invention is not limited thereto but may be otherwise variously embodied and practiced within the scope of the following claims.

The invention claimed is:

1. A device for an impedance-based probing of materials comprising:
   at least one coil,
   a pulse generator for generating current pulses in said coil; and
   a measurement unit for determining a parameter indicative of an impedance of said coil,
   wherein said device comprises a two-dimensional array of coils arranged in rows and columns,
   wherein said measurement unit is adapted to determine said parameter for individual ones of said coils,
   wherein said pulse generator is adapted to feed individual current pulses to each of said coils, and
   wherein said pulse generator comprises:
      row pulse lines, with one row pulse line arranged along each row,
      column pulse lines, with one column pulse line arranged along each column,
      first semiconductor switches,
      wherein one first semiconductor switch is attributed to each coil and each first semiconductor switch comprises a first and a second current terminal and a control terminal,
      wherein a conductivity between said first and said second current terminal is controlled by a voltage at said control terminal, and
      wherein said coils and said row pulse lines are connected to said current terminals and said column pulse lines are connected to said control terminals.

2. The device of claim 1, wherein said coils are arranged on a flat or curved plane with a first number N1>2 of said coils being arranged along a column direction and a second number N2>2 of said coils being arranged along a row direction, with the row and column directions extending transversally to each other.

3. The device of claim 1 further comprising second semiconductor switches,
   wherein said measurement unit comprises an amplifier, and each of said second semiconductor switches is arranged between one of said coils and said amplifier for connecting a single one or a subset of said coils to said amplifier.

4. The device of claim 3, wherein one second semiconductor switch is attributed to each coil.

5. The device of claim 1, wherein one second semiconductor switch is attributed to each coil, said device further comprising column signal lines,
   wherein said second semiconductor switch comprises a first and a second current terminal and a control terminal,
   wherein a conductivity between said first and said second current terminal is controlled by a voltage at said control terminal, and
   wherein, for said second semiconductor switch
      said control terminal is connected to said row pulse line,
      said first current terminal is connected to said coil, and
      said second current terminal is connected to one of said column signal lines.

6. The device of claim 5, further comprising a resistor arranged between said first current terminal of said second semiconductor switch and said coil.

7. The device of claim 5, further comprising a demultiplexer between said column signal lines and said amplifier adapted to connect a single one of said column signal lines to said amplifier.

8. The device of claim 4, further comprising a voltage limiter arranged at an input of said amplifier and adapted to keep a voltage at said input below a maximum allowable voltage between said current terminals and said control terminal of said second semiconductor switches.

9. The device of claim 1, wherein said coils are formed by conductive tracks on a printed circuit board.

10. The device of claim 9, wherein said printed circuit board comprises a plurality of layers, wherein each coil is formed by conductive tracks on several of said layers.

11. A method for probing concrete with the device of claim 1, comprising:
   generating current pulses in each coil
   determining a parameter of the probed concrete that is indicative of an impedance for each coil.

12. The device of claim 2, wherein the row and column directions extend perpendicularly to each other.

13. The device of claim 6, wherein said resistor has a resistance of at least 10-1000Ω.

14. The device of claim 8, wherein the voltage limiter is adapted to keep the voltage at said input below 100 Volts.

15. The method of claim 11, wherein the probed concrete is reinforced concrete.

16. A device for an impedance-based probing of materials having
   a two-dimensional array of coils arranged in rows and columns,
   a pulse generator for generating current pulses in said coil and
   a measurement unit for determining a parameter indicative of an impedance of said coil, wherein said measurement unit is adapted to determine said parameter for individual ones of said coils, wherein said pulse generator comprises row pulse lines, with one row pulse line arranged along each row, column pulse lines, with one column pulse line arranged along each column, first semiconductor switches, wherein one first semiconductor switch is attributed to each coil and wherein each first semiconductor switch comprises a first and a second current terminal and a control terminal, wherein a conductivity between said first and said second current terminal is controlled by a voltage at said control terminal, wherein said coils and said row pulse lines are connected to said current terminals and said column pulse lines are connected to said control terminals.

\* \* \* \* \*